United States Patent [19]

Kaeding

[11] 4,128,592
[45] Dec. 5, 1978

[54] SELECTIVE PRODUCTION OF PARA DIALKYL BENZENE

[75] Inventor: Warren W. Kaeding, Westfield, N.J.

[73] Assignee: Mobil Oil Corporation, New York, N.Y.

[21] Appl. No.: 854,454

[22] Filed: Nov. 23, 1977

[51] Int. Cl.² ............................ C07C 3/52; C07C 3/62
[52] U.S. Cl. ................................ 260/671 C; 252/435; 252/455 Z; 260/671 R; 260/672 T
[58] Field of Search ............ 260/671 R, 671 C, 672 T; 252/455 Z, 435

[56] References Cited

U.S. PATENT DOCUMENTS

| | | | |
|---|---|---|---|
| 3,965,209 | 6/1976 | Butler | 260/671 C |
| 4,001,346 | 1/1977 | Chu | 260/671 R |
| 4,011,276 | 3/1977 | Chu | 260/672 T |
| 4,034,053 | 7/1977 | Kaeding | 260/672 T |

Primary Examiner—Delbert E. Gantz
Assistant Examiner—C. E. Spresser
Attorney, Agent, or Firm—Charles A. Huggett

[57] ABSTRACT

A catalytic process is provided for the selective production of the para isomer of the compound:

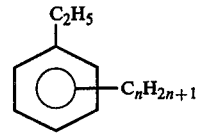

where n is 1 or 2 by contacting a hydrocarbon precursor selected from the group consisting of ethylbenzene and mixtures of ethylbenzene or toluene with ethylene, under conversion conditions, which entail disproportionation of the ethylbenzene or alkylation of the ethylbenzene or toluene with ethylene, in the presence of a catalyst comprising a crystalline aluminosilicate zeolite, characterized by a silica to alumina ratio of at least about 12, a constraint index, as hereinafter defined, within the approximate range of 1 to 12 and a minimum crystal dimension greater than about 0.5 micron, which zeolite has undergone prior sequential treatment including:

(1) steaming at a temperature of between about 250 and about 1000° C for a period of at least 0.5 hour;
(2) impregnation with at least about 0.25 weight percent of phosphorus oxide;
(3) impregnation with at least about 0.25 weight percent of magnesium oxide and
(4) coking to deposit at least about 1 weight percent of coke thereon to yield a resulting reaction product mixture in which the para isomer of said compound is present in an amount exceeding 99 percent of the total of said compound produced.

16 Claims, No Drawings

SELECTIVE PRODUCTION OF PARA DIALKYL BENZENE

BACKGROUND OF THE INVENTION

1. Field of the Invention

This invention relates to a process for selectively producing para-ethyltoluene or para-diethylbenzene in an amount and of a quality which can be subsequently directly oxidized to terephthalic acid without the necessity of intermediate purification.

2. Description of the Prior Art

Terephthalic acid is an important chemical, representing an intermediate in the manufacture of synthetic fibers such as "Dacron". It has heretofore been commercially produced by oxidation of para-xylene employing various oxidation techniques. A significant cost, both for capital and operation, to obtain a product of greater than 99 percent para-xylene of fiber grade quality has necessitated expensive separation and purification steps to remove close boiling by-products. In addition, a costly step has generally been required to isomerize the ortho- and meta-isomers to the desired para and to remove ethylbenzene prior to subjecting the para-xylene product to oxidation.

Alkylation of aromatic hydrocarbon utilizing crystalline aluminosilicate catalysts has heretofore been described. U.S. Pat. No. 2,904,697 to Mattox refers to alkylation of aromatic hydrocarbons with an olefin in the presence of a crystalline metallic aluminosilicate having uniform openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

The disproportionation of aromatic hydrocarbons in the presence of zeolite catalysts has been described by Grandio et al. in the *Oil and Gas Journal*, Vol. 69, No. 48 (1971). U.S. Pat. Nos. 3,126,422; 3,413,374; 3,598,878; 3,598,879 and 3,607,961 show vapor-phase disproportionation of toluene over various catalysts.

While the above-noted prior art is considered of interest in connection with the subject matter of the present invention, the conversion process described herein, utilizing a crystalline aluminosilicate zeolite catalyst of specified characteristics which has undergone a particular preliminary treatment involving steaming, impregnation with phosphorus, followed by impregnation with magnesium and controlled pre-coking has not, insofar as is known, been heretofore described.

SUMMARY OF THE INVENTION

In accordance with the present invention, there has been discovered a process for the selective production of the para isomer of the compound:

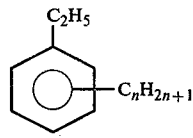

where $n$ is 1 or 2 in an amount greater than 99 percent of the total of said compound produced, which can either directly or after removal of easily separable by-products, be oxidized to terephthalic acid without the need for an expensive separation and/or isomerization step characteristic for para-xylene production and purification to a product of fiber grade quality.

The process of the invention involves contacting a hydrocarbon precursor selected from the group consisting of ethylbenzene and mixtures of ethylbenzene or toluene with ethylene, under conversion conditions to effect disproportionation of the ethylbenzene or alkylation of the ethylbenzene or toluene with ethylene in the presence of a particularly specified catalyst comprising a crystalline aluminosilicate zeolite having a silica to alumina mole ratio of at least about 12, a constraint index within the approximate range of 1 to 12 and a minimum crystal dimension greater than about 0.5 micron.

The specified catalyst, in accordance with the present invention, has necessarily undergone a series of preliminary treating steps including steaming at a temperature between about 250° and about 1000° C. for at least about 0.5 hour and generally between about 0.5 and about 100 hours. The steamed catalyst is then impregnated with at least about 0.25 weight percent and generally not more than about 25 weight percent of phosphorus oxide, followed by impregnation with at least about 0.25 weight percent and generally not more than about 25 weight percent of magnesium oxide. The steamed, so impregnated catalyst is thereafter subjected to a coking treatment to deposite at least about 1 and up to about 50 weight percent of coke thereon.

The final catalyst has been found to be particularly applicable in effecting conversion of a hydrocarbon precursor charge selected from ethylbenzene or a mixture of ethylbenzene or toluene with ethylene to selectively produce para diethylbenzene or para ethyltoluene in an amount approaching 100 percent of the total dialkyl benzene product produced.

Conversion of the hydrocarbon precursor charge is effected at a temperature between about 250 and about 750° C. at a pressure between about 0.1 and about 100 atmospheres utilizing a feed weight hourly space velocity (WHSV) between about 0.1 and about 200. The latter WHSV is based upon the weight of catalyst composition, i.e., total weight of active catalyst and binder therefor.

When ethylbenzene is the selected hydrocarbon precursor, disproportionation thereof to diethylbenzene and benzene is generally carried out at a temperature between about 400° C. and about 750° C. at a pressure between about 1 atmosphere and about 100 atmospheres utilizing a weight hourly space velocity of between about 1 and about 50.

In effecting alkylation of ethylbenzene or toluene with ethylene, conversion conditions include a temperature between about 250° C. and about 600° C., pressure between about 0.1 and about 100 atmospheres, utilizing a feed weight hourly space velocity between about 0.1 and about 100 and a molar feed ratio of ethylbenzene or toluene/ethylene between about 1 and about 10.

The para-ethyltoluene or para-diethylbenzene realized in accordance with the process described herein can be oxidized to terephthalic acid directly under conditions similar to those employed in producing such acid by oxidation of para-xylene.

DESCRIPTION OF SPECIFIC EMBODIMENTS

The hydrocarbon precursor undergoing selective conversion to the para isomer of the compound:

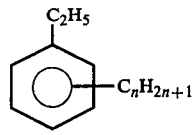

where n is 1 or 2 in accordance with the process of this invention, is ethylbenzene or a mixture of ethylbenzene or toluene with ethylene.

The above charge is brought into contact, under conversion conditions, with a bed comprising particleform catalyst containing a crystalline aluminosilicate having: a silica to alumina mole ratio of at least 12, a constraint index within the approximate range of 1 to 12 and a minimum crystal dimension of greater than about 0.5 micron.

Generally, the crystal size of the aluminosilicate zeolite employed is between about 1 and about 20 microns and preferably within the approximate range of 1 to 6 microns. It is an important feature of the catalyst employed in the process of the invention that the crystal size of the zeolite be greater than about 0.5 micron, since the use of a comparable zeolite but of smaller crystal size did not afford the desired selective production of the para isomer of diethylbenzene or ethyltoluene achieved with the catalyst described herein.

Such comprises a crystalline aluminosilicate zeolite which is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log 10 \text{ (fraction of n-hexane remaining)}}{\log 10 \text{ (fraction of 3-methylpentane remaining)}}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |

| CAS | C.I. |
|---|---|
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F. to 950° F., the constraint index will have a value for any given zeolite of interest herein with the approximate range of 1 to 12.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35 with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

Generally, however, the zeolite either directly or via initial ammonium exchange followed by calcination, is preferably hydrogen exchanged such that a predominate proportion of its exchangeable cations are hydrogen ions. In general, it is contemplated that more than 50 percent and preferably more than 75 percent of the cationic sites of the crystalline aluminosilicate zeolite will be occupied by hydrogen ions.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families includes the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The above crystalline alumonosilicate zeolites employed are subjected to a sequential series of preliminary treatments before catalytic use thereof. The first pretreatment involves contact of the zeolite with an atmosphere containing from about 5 to about 100 percent steam at a temperature of from about 250° C. to about 1000° C. for a period of at least about 0.5 and generally between about 0.5 and about 100 hours under pressures ranging from sub-atmospheric to several hundred atmospheres. Preferably, steam treatment is effected at a temperature between about 400° C. and about 700° C. for a period of between about 1 and about 24 hours.

The steamed zeolite product is then impregnated with phosphorus oxide in an amount of at least 0.25 weight percent but generally not more than about 25 weight percent. Impregnation can readily be effected by contacting the zeolite with a solution of an appropriate phosphorus compound, followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $PPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tribuytylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RA)PR_2$ and $(RS)_2PR$. Examples of phosphite esters include trimethylphosphite, triethylphosphite, diisopropylphosphite, butylphosphite; and pyrophosphites such as tetraethylpyrophosphate. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphonic acid, diethylchloro thiophosphate, methyl acid phosphate and other alcohol-$P_2O_5$ reaction products.

Particularly preferred are ammonium phosphates including ammonium monohydrogen phosphate $(NH_4)_2HPO_4$ and ammonium dihydrogen phosphate $NH_4H_2PO_4$.

Reaction of the zeolite with the phosphorus compound is effected by contacting the zeolite with such compound. Where the treating phosphorus compound is a liquid, such compound can be in a solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation is also preferred. The heating can be carried out in the presence of oxygen, for example, air. Heating can be at a temperature of about 150° C. However, higher temperatures, i.e., up to about 500° C. are preferred. Heating is generally carried out for 3–5 hours but may be extended to 24 hours or longer. While heating temperatures above about 500° C. can be employed, they are not necessary. At temperatures of about 1000° C., the crystal structure of the zeolite tends to deteriorate.

The amount of phosphorus incorporated with the zeolite should be at least about 0.25 percent by weight. However, it is preferred that the amount of phosphorus in the zeolite be at least about 2 percent by weight when the same is combined with a binder, e.g., 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

The zeolite containing phosphorus oxide is then further combined with magnesium oxide by contact with a suitable compound of magnesium. Representative magnesium-containing compounds include magnesium acetate, magnesium nitrate, magnesium benzoate, magnesium proprionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium silicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e., may be used as a neat liquid. Where the treating compound is in the gaseous phase, it can be used by itself or can be used in admixture with a gaseous diluent relatively inert to the treating compound and the zeolite such as helium or nitrogen or with an organic solvent, such as octane or toluene.

Heating of the magnesium compound impregnated catalyst subsequent to preparation is preferred. The heating can be carried out in the presence of oxygen, for example, air. Heating can be at a temperature of about 150° C. However, higher temperatures, i.e., up to about 500° C. are preferred. Heating is generally carried out for 1–5 hours but may be extended to 24 hours or longer. While heating temperatures above about 500° C. may be employed, they are generally not necessary. At temperatures of about 1000° C., the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g., 35 weight percent of alumina. The amount of magnesium oxide can be as high as about 25 percent by weight or more depending on the amount and type binder present. Preferably, the amount of magnesium oxide added to the zeolite is between about 1 and about 15 percent by weight.

The amount of magnesium oxide incorporated with the zeolite by reaction with the treating solution and subsequent calcination in air will depend on several factors. One of these is the reaction time, i.e., the time that the zeolite and the magnesium-containing source are maintained in contact with each other. With greater reaction times, all other factors being equal, a greater amount of magnesium oxide is incorporated with the zeolite. Other factors upon which the amount of magnesium oxide incorporated with the zeolite is dependent include reaction temperature, concentration of the treating compound in the reaction mixture, the degree to which the zeolite has been dried prior to reaction with the treating compound, the conditions of drying of the zeolite after reaction of the zeolite with the magnesium compound and the amount and type of binder incorporated with the zeolite.

After contact of the phosphorus oxide-containing zeolite with the magnesium reagent, the resulting composite is dried and heating in a manner similar to that used in preparing the phosphorus oxide-containing zeolite.

Coking of the steamed, phosphorus oxide, magnesium oxide — impregnated zeolite can be carried out by contacting with a thermally decomposable organic compound, e.g., toluene, at a temperature in excess of the decomposition temperature of said compound, generally greater than 500° C., but less than 650° C., at a hydrogen to organic compound mole ratio between 0 and 1 to deposit at least about 1 weight percent coke thereon. Usually, between about 1 and about 50 weight percent and preferably between about 5 and about 40 weight percent of coke is deposited on the catalyst prior to use of the same in selective production of para-ethyltoluene or para-diethyltoluene.

For toluene and organic compounds of similar reactivity, the temperature employed is greater than 500° C. With organic compounds that are more readily decomposable than toluene, such as, for example, phenols and styrene, coking can be carried out at temperatures less than 500° C. With the use of higher temperatures in the aforenoted range, the presence of hydrogen has not been found necessary. With temperatures of less than about 550° C., preferably some hydrogen, generally at least 0.2 mole of hydrogen per mole of organic compound is desirable to yield a more stable catalyst.

Organic materials, thermally decomposable under the above temperature conditions to provide coke depositions, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an allyl-substituted aromatic and particularly toluene will be the source of coke. Toluene or ethylbenzene are particularly desirable because they are effective and are the feeds utilized for the alkylation or disproportionation reaction. In a commercial operation, it would not be necessary to introduce another hydrocarbon catalyst coking reagent to the system and therefore eliminate the need to have separate tanks and associated piping for feed and product.

The conversion process described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g., air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5-2%) is used to burn the coke in a controlled manner so as to limit the temperature to a maximum of around 500°-550° C.

The following examples will serve to illustrate the process of this invention without limiting the same.

EXAMPLE 1

HZSM-5 zeolite (60.5 grams) having a crystal size of about 2 microns in the form of 1/16 inch diameter extrudate with a 35 weight percent alumina binder was steamed at 600° C. for 1 hour. The steamed material was then impregnated with a solution of 38.7 grams of diammonium acid phosphate in 100 ml. of water, dried and calcined at 500° C. for about 16 hours in an open dish. The resulting product was cooled and impregnated with a solution of 195 grams of magnesium acetate tetrahydrate in 133 ml. of water, dried and calcined at 500° C. for about 19 hours. The final catalyst contained 4.93 weight percent magnesium, present as the oxide, and 3.48 weight percent phosphorus, present as the oxide.

EXAMPLE 2

Alkylation of toluene with ethylene to produce ethyltoluene in the vapor phase was carried out at a temperature of 425° C. and a pressure of 100 psig in the presence of hydrogen using the catalyst of Example 1. The conditions of reaction and results obtained are summarized in Table I below:

TABLE I

| Run No. | Temp °C | Pressure psig | Run Time Hrs. | Feed Toluene/$C_2H_4$/$H_2$ WHSV (Mole Ratio) | Conversion, % Toluene | Conversion, % $C_2H_4$ | Para-Ethylene Total Ethyltoluene % | Selectivity, wt. % Ethyltoluene | Selectivity, wt. % Light Gas | Selectivity, wt. % Other Aromatics |
|---|---|---|---|---|---|---|---|---|---|---|
| 1 | 425 | 100 | 22 | 29.3/1.2/.24 | 10.5–10* | 85–77 | 95.9–96.3 | 90.2–95.1 | 1.2–1.0 | 8.6–3.8 |
| 1a | 425 | 100 | 140 | 29.3/1.2/.24 (7.7–1–3) | 10.5–9.3 | 85–71 | 95.9–96.4 | 90.2–96.9 | 1.2–.7 | 8.6–2.5 |
| Selectivate Catalyst | | | | | | | | | | |
| 2 | 425 | 100 | 25 | 29.3/1.2/.24 | 5.2–3.7 | 46–34 | 99.9** | 96.0–95.2 | 1.7–1.4 | 2.3–3.4 |
| Regenerate Catalyst | | | | | | | | | | |
| 3 | 425 | 100 | 21 | 29.3/1.2/.24 (7.7–1–3) | 5.0–2.5 | 46–23 | 99.9** | 95.4–95.5 | 2.1–2.4 | 2.5–2.1 |
| Calcine (Regenerate) Catalyst | | | | | | | | | | |
| 4 | 425 | 100 | 2 | 29.3/1.2/.24 (7.7–1–3) | 10.4 | 87–85 | 96.6 | 91.2–92.7 | 2.3–1.8 | 6.5–5.5 |

*Range shows value for first and last hour of the run for total time indicated.
**Level obtained throughout entire run period.

It will be seen from Runs 1 and 1a of the above tabulated data that a high degree of toluene conversion was maintained throughout the entire period of operation, the theoretical maximum toluene conversion being 13 percent based on limiting ethylene feed. The amount of para isomer in the ethyltoluene produced was 95.9–96.4 weight percent. The balance of ethyltoluene was the meta isomer, since none of the ortho isomer was detected.

The other aromatic products produced included benzene, ethylbenzene, para and meta xylene, together with a trace of diethylbenzene. The light gas produced was composed primarily of unreacted ethylene, along with small amounts of methane, ethane, propylene, propane and benzenes.

The ethyltoluene product could be separated and purified by a simple distillation. However, further purification to increase the amount of para-ethyltoluene above 99 percent would be very difficult by ordinary methods because of the very low freezing points and proximity of the boiling points of the para and meta isomer of ethyltoluene as noted below:

| | Boiling Point °C. at 760 mm. | Melting Point °C. |
|---|---|---|
| Para-Ethyltoluene | 161.989 | −62.350 |
| Meta-Ethyltoluene | 161.305 | −95.570 |

EXAMPLE 3

After completion of Runs 1 and 1a, the catalyst used was treated, in the same apparatus used for the alkylation, for 21 hours with a mixture of toluene and hydrogen in a mole ratio of 7.7 toluene/1 hydrogen at 600° C. and a pressure of 100 psig using a weight hourly space velocity of 29.2 toluene/0.08 hydrogen.

When the alkylation of toluene with ethylene was resumed after this catalyst treatment, it will be seen, from Run 2 of Table I, that a dramatic increase in selectivity to the desired para-ethyltoluene isomer was achieved. Although very high selectivity to the desired product was maintained (96-95%), the conversion of the starting materials was reduced. The ethyltoluene product obtained was sufficiently high in the desired para isomer, that a simple distillation produced a product which could be directly oxidized to fiber grade terephthalic acid.

The catalyst was capable of regeneration by treatment with hydrogen at 550° C., 100 psig, WHSV of .24 for 2 hours to restore the initial high selectivity to para-ethyltoluene, as shown in Run 3 of Table I. A conventional regeneration of the catalyst by exposure to air at 550° C. and atmospheric pressure for 13 hours served to restore the catalyst performance to that observed initially, as will be evident from a comparison of the results obtained in Runs 1 to 4 of Table I.

EXAMPLE 4

The catalyst after calcination with air (Run 4, Table I) was treated with hydrogen and toluene, such treatment being referred to as "selectivation", at 600° C., 100 psig for 2.75 hours using a toluene/hydrogen mole ratio feed of 7.7/1 and a toluene/hydrogen WHSV of 30.1/0.08 to improve the selectivity to the para isomer. The results obtained are shown in Table II below:

centration of 99.8 percent para isomer in the ethyltoluene product.

When the temperature was increased from 425° to 450° C., conversion and aging improved with virtually no penalty in selectivity to the desired para isomer as will be evident from the results obtained in Runs 8 and 8a.

Finally, a 4 hour regeneration of the catalyst with hydrogen at 550° C., 100 psig. and a WHSV of 0.24 restored catalyst activity and performance to the initial value as will be seen from Run 9 in the above Table.

From the results, it is evident that a simple distillation of the liquid product will easily separate ethyltoluene from the starting material and minor side reaction products. Thus, after selectivation for about 8 hours, the concentration of para isomer was 99.2-99.8 percent, a value sufficiently high to be used for oxidation to fiber grade terephthalic acid by conventional methods. A costly purification of the type presently required to prepare fiber grade para-xylene has thus been eliminated.

EXAMPLE 5

Alkylation of ethylbenzene with ethylene to produce diethylbenzene was carried out in the presence of the catalyst of Example 1 which had been used in Examples 2-4 and then calcined at a temperature of 550° C. in air

TABLE II

| Run No. | Temp ° C | Pressure psig | Run Time Hrs. | Feed Toluene/$C_2H_4$/$H_2$ WHSV (Mole Ratio) | Conversion, % Toluene | $C_2H_4$ | Para-Ethylene Total Ethyltoluene % | Selectivity, wt. % Ethyltoluene | Light Gas | Other Aromatics |
|---|---|---|---|---|---|---|---|---|---|---|
| 5 | 425 | 100 | Selective Catalyst - 2.75 Hrs. 18 30.1/1.2/.24 | 9.9-9.4* | 80-74* | 98.0 | 95.1-97.1 | 1.0-.6 | 3.9-2.3 |
| 6 | 425 | 100 | Selective Catalyst - 5.0 Hrs. 18 30.1/1.2/.24 | 9.6-8.5 | 78-67 | 99.2 | 95.4-97.5 | 1.0-.6 | 3.7-2.0 |
| 7 | 425 | 100 | Selective Catalyst - 3.0 Hrs. 20 30.1/1.2/.24 | 8.7-6.8 | 73-56 | 99.8 | 95.6-97.7 | 1.2-.6 | 3.2-1.7 |
| 8 | 450 | 100 | 36 | 30.1/1.2/.24 | 6.8-7.3 | 56-59 | 99.7 | 97.7-96.1 | .6-.7 | 1.7-3.2 |
| 8a | 450 | 100 | 117 | 30.1/1.2/.24 | 6.8-5.9 | 73-44 | 99.8-99.7 | 95.6-97.2 | 1.2-.7 | 3.2-2.1 |
| 9 | 450 | 100 | Regenerate Hydrogen - 4 Hrs. 67 30.1/1.2/.24 | 8.3-6.2 | 66-54 | 99.6 | 92.0-97.4 | 3.8-.6 | 4.3-1.9 |

*Range shows value for first and last hour of the run for total time indicated.

It will be seen from the results of Run 5 that after 2.75 hours of selectivation, the para isomer content in the ethyltoluene product has increased to 98 percent. An additional selectivation of 5 hours, under the above conditions, increased the amount of para-ethyltoluene to 99.2 percent, as will be seen from the results of Run 6 in the above Table. An additional selectivation treatment of the catalyst under the above conditions, for 3 hours, amounting to a total of 10.75 hours, gave a conat atmospheric pressure for about 20 hours. The reaction conditions employed and the results obtained are summarized in Table III below:

TABLE III

| Run No. | Temp ° C. | Pressure psig | Run Time Hrs. | Feed Ethylbenzene/$C_2H_4$/$H_2$ WHSV (Mole Ratio) | Conversion % Ethyl-benzene | $C_2H_4$ | Para-Diethylbenzene Total Diethylbenzene | Selectivity, Wt.% Diethyl-benzene | Benzene | Light Gas | Other Aromatics |
|---|---|---|---|---|---|---|---|---|---|---|---|
| 1 | 425 | 100 | 23 | 29.7/1.2/.24 | 21.9-18.6* | 65-58 | 98.4-98.6 | 71.5-78.2 | 20.5-18.1 | 2.6-8 | 5.4-2.9 |
| 2 | 425 | 100 | 27 | 29.7/1.2/.24 (6.8/1/3) | 18.6-16.3 | 58-55 | 98.6-98.9 | 78.2-80.0 | 18.1-16.6 | .8-.7 | 2.9-2.7 |
| 3 | 425 | 100 | Selective Catalyst - 11 Hours 21 30.2/1.2/.24 (6.9/1/3) | 14.3-8.8 | 54-38 | 99.8 | 76.8-79.9 | 17.7-14.0 | 1.6-.6 | 3.9-5.5 |
| 4 | 425 | 100 | 23 | 30.2/1.2/.24 | 8.8-3.9 | 38-21 | 99.8-99.9 | 79.9-75.9 | 14.0-13.8 | .6-.5 | 5.5-9.8 |
| 5 | 475 | 100 | Regenerate Hydrogen - 4 Hours 1 30.2/0/.24 (6.9/0/3) | 17.7 | — | 99.6 | 31.6 | 50.4 | 13.3 | 4.7 |
| 6 | 525 | 100 | 19 | 30.2/0/.24 (6.9/0/3) | 23.4-18.0 | — | 99.3 | 15.9-15.5 | 60.2-61.1 | 17.5-18.9 | 6.5-4.4 |
| 7 | 525 | 100 | 1 | 30.2/1.2/.24 (6.9/1/3) | 15.2 | 29 | 99.6 | 32.7 | 58 | 3.1 | 6.2 |

*Range shows value for first and last hour of the run for total time indicated.

As will be seen from Runs 1 and 2 in the above Table, high concentrations of the para isomer (98.4-98.9%) in the diethyltoluene product were obtained over a two day period of operation.

EXAMPLE 6

The catalyst used in Example 5 was selectivated for about 11 hours by treatment with a toluene/hydrogen feed, the mole ratio of toluene to hydrogen being 7.7/1, as a temperature of 600° C., a pressure of 100 psig at a toluene/hydrogen WHSV of 29.2/0.08 and then used for alkylation of ethylbenzene with ethylene under the conditions shown in Table III.

It will be seen from the results of Runs 3 and 4 of such table that the amount of para isomer in the diethylbenzene product increased to 99.8–99.9 percent. This product is immediately satisfactory for oxidation to fiber grade terephthalic acid without the need for a special purification step to remove meta isomer, no ortho isomers being detected in the diethylbenzene product.

EXAMPLE 7

The catalyst used in Example 6 was regenerated with hydrogen at 550° C., 100 psig pressure at a WHSV of 0.24 for 4 hours and thereafter tested for its ability to disproportionate ethylbenzene in the presence of hydrogen. The conditions and results are shown for Runs 5–7 of Table III. In Run 5, the para isomer in the diethylbenzene product was sufficiently high (99.6%) to meet fiber grade specifications. In Run 6, conversion was increased by increasing the temperature to 525° C. with only a slight reduction in para-diethylbenzene concentration (99.3%). The major product, however, was benzene, a coproduct expected from the disproportionation. From Run 7, will be seen that cofeeding ethylene doubled the selectivity to diethylbenzene by comparison with the previous run.

EXAMPLE 8

A mixture of 0.20 moles of para-ethyltoluene, 0.03 mole of cobaltic acetate, 0.10 mole of methyl ethyl ketone and 2.30 moles of glacial acetic acid were placed in a stainless steel, one liter autoclave. Two moles of liquid n-butane were pumped into the autoclave and oxygen added to obtain a pressure of 420 psig. The temperature was increased to 130° C. with stirring and the pressure also increased to 700 psig. When the oxidation began, cooling was necessary to maintain the desired temperature of 130° C. Additional oxygen was also supplied to maintain the desired pressure of 700 psig. When oxidation ceased the autoclave was cooled, depressurized and the contents analyzed.

A 97 percent yield of aromatic carboxylic acid was obtained based on starting para-ethyltoluene. Of this, 90 percent was terephthalic acid, 4 percent acetylbenzoic acid and 6 percent unidentified material. This experiment shows that oxidation of para-ethyltoluene produces terephthalic acid in a manner similar to that observed for para-xylene.

It is to be understood that the foregoing description is merely illustrative of preferred embodiments of the invention, of which many variations may be made by those skilled in the art within the scope of the following claims without departing from the spirit thereof.

What we claim is:

1. Process for selectively producing the para isomer of the compound:

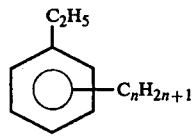

where $n$ is 1 or 2 which comprises contacting a hydrocarbon precursor selected from the group consisting of ethylbenzene and mixtures of ethylbenzene or toluene with ethylene in which the molar ratio of ethylbenzene or toluene to ethylene is between about 1 and about 10, under conversion conditions, in the presence of a catalyst comprising a crystalline aluminosilicate zeolite, characterized by a silica to alumina mole ratio of at least about 12, a constraint index within the approximate range of 1 to 12 and a minimum crystal dimension greater than about 0.5 micron, said zeolite having undergone the following prior sequential treatment:
  (1) steaming at a temperature of between about 250° and about 1000° C. for a period of at least 0.5 hour;
  (2) impregnation with at least about 0.25 weight percent of phosphorus oxide;
  (3) impregnation with at least about 0.25 weight percent of magnesium oxide and
  (4) coking for deposition of at least about 1 weight percent of coke thereon to yield a resulting reaction product mixture in which the para isomer of said compound is present in an amount exceeding 99 percent of the total of said compound produced.

2. The process of claim 1 wherein said conversion conditions include a temperature between about 250° C. and about 750° C., a pressure between about 1 and about 100 atmospheres and a weight hourly space velocity between about 0.1 and about 200.

3. The process of claim 1 wherein said hydrocarbon precursor is ethylbenzene.

4. The process of claim 1 wherein said hydrocarbon precursor is a mixture of ethylbenzene or toluene and ethylene.

5. The process of claim 3 wherein said conversion conditions include a temperature between about 400° C. and about 750° C., a pressure between about 1 atmosphere and about 100 atmospheres and a weight hourly space velocity between about 1 and about 50.

6. The process of claim 4 wherein said conversion conditions include a temperature between about 250° C. and about 600° C., a pressure between about 0.1 and about 100 atmospheres and a weight hourly space velocity between about 1 and about 10.

7. The process of claim 1 wherein said steaming is carried out at a temperature between about 400° C. and about 700° C. for a period of between about 1 and about 24 hours.

8. The process of claim 1 wherein said impregnation with phosphorus oxide is in an amount between about 0.7 and about 15 weight percent.

9. The process of claim 1 wherein said impregnation with magnesium oxide is in an amount between about 1 and about 15 percent.

10. The process of claim 1 wherein said coking deposits between about 1 and about 50 weight percent of coke.

11. The process of claim 1 wherein said coking deposits between about 5 and about 40 weight percent of coke.

12. The process of claim 1 wherein said crystalline aluminosilicate zeolite is ZSM-5.

13. The process of claim 1 wherein said crystalline aluminosilicate zeolite is admixed with a binder therefor.

14. The process of claim 12 wherein said ZSM-5 is admixed with a binder therefor.

15. The process of claim 1 wherein said compound is para-ethyltoluene.

16. The process of claim 1 wherein said compound is para-diethylbenzene.

* * * * *

UNITED STATES PATENT AND TRADEMARK OFFICE
CERTIFICATE OF CORRECTION

PATENT NO. : 4,128,592

DATED : December 5, 1978

INVENTOR(S) : Warren W. Kaeding

It is certified that error appears in the above-identified patent and that said Letters Patent are hereby corrected as shown below:

Column 2, line 32    "deposite" should be -- deposit --

Column 11, line 31   "allyl-substituted" should be -- alkyl-substituted --

Signed and Sealed this

Twenty-fourth Day of April 1979

[SEAL]

Attest:

RUTH C. MASON
*Attesting Officer*

DONALD W. BANNER
*Commissioner of Patents and Trademarks*